United States Patent [19]

Nagatsu et al.

[11] 4,371,514

[45] Feb. 1, 1983

[54] RADIOIMMUNOASSAY OF PTERINS AND NOVEL PTERIN DERIVATIVES USEFUL THEREFOR

[75] Inventors: Toshiharu Nagatsu; Takeshi Kato, both of Yokohama; Tokio Yamaguchi, Hachioji; Miki Akino, Musashino; Sadao Matsuura, Nagoya; Takashi Sugimoto, Chiryu, all of Japan

[73] Assignee: Daiichi Radioisotope Laboratories, Ltd., Tokyo, Japan

[21] Appl. No.: 166,519

[22] Filed: Jul. 7, 1980

[30] Foreign Application Priority Data

Jul. 4, 1979 [JP] Japan .................. 54/84568
Jan. 11, 1980 [JP] Japan .................. 55/18841

[51] Int. Cl.³ .................. G01N 33/56; G01N 33/58; C07D 475/00
[52] U.S. Cl. .................. 424/1; 544/258; 436/538; 436/540; 436/542
[58] Field of Search .................. 544/258; 424/1, 12; 23/230 B

[56] References Cited

U.S. PATENT DOCUMENTS

| | | | |
|---|---|---|---|
| 3,972,991 | 8/1976 | Caston et al. | 424/1 |
| 3,988,431 | 10/1976 | Givas et al. | 424/1.5 |
| 3,989,812 | 11/1976 | Barrett et al. | 424/1 |
| 4,028,465 | 6/1977 | Lewin et al. | 424/1 |
| 4,091,087 | 5/1978 | Barrett et al. | 424/1 |
| 4,115,065 | 9/1978 | Bayly et al. | 23/230.6 |
| 4,135,880 | 1/1979 | Mangiardi et al. | 23/230 B |
| 4,136,159 | 1/1979 | Stone | 424/1 |
| 4,146,602 | 3/1979 | Gutcho et al. | 424/1 |
| 4,202,976 | 5/1980 | Bayly et al. | 544/258 X |
| 4,276,280 | 6/1981 | Akerkar et al. | 544/258 X |

FOREIGN PATENT DOCUMENTS

| | | | |
|---|---|---|---|
| 2741677 | 3/1978 | Fed. Rep. of Germany | 424/1 |
| 785352 | 10/1957 | United Kingdom | 544/258 |
| 785353 | 10/1957 | United Kingdom | 544/258 |

Primary Examiner—Christine M. Nucker
Attorney, Agent, or Firm—Sughrue, Mion, Zinn, Macpeak & Seas

[57] ABSTRACT

Pterin derivatives are described having the formula (I)

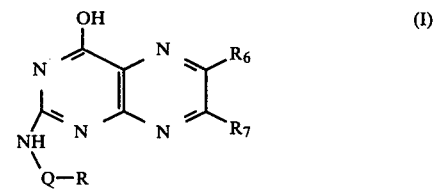

wherein R represents a hydroxyphenyl group, a radioiodinated hydroxyphenyl group, a tyraminocarbonyl group, a radioiodinated tyraminocarbonyl group, a proteinocarbonyl group or a carboxy group; Q represents a straight or branched chain alkylene group having 1 to 6 carbon atoms; and $R_6$ and $R_7$ each represents a hydrogen, an alkyl group having from 1 to 6 carbon atoms, a hydroxyalkyl group having from 1 to 6 carbon atoms; and a radioimmunoassay method is described using a radioiodinated 4-hydroxy-2-tyraminopteridine derivative or a radioiodinated 4-hydroxy-2-tyraminocarbonylalkylaminopteridine derivative as the tracer.

16 Claims, 2 Drawing Figures

RADIOIMMUNOASSAY OF PTERINS AND NOVEL PTERIN DERIVATIVES USEFUL THEREFOR

BACKGROUND OF THE INVENTION

1. Field of the Invention

This invention relates to novel pterin derivatives and to a radioimmunoassay (hereinafter "RIA") method for determining pterins using a pterin derivative containing a radioiodinated tyramine moiety as the tracer.

2. Description of the Prior Art

In recent years, it has been found that pterins, such as folic acid, play a role as a coenzyme in amino acid-metabolism. Thid finding led to a concept that the detection of quantitative changes of pterins in a living body could be useful for the diagnosis of various enzyme deficiencies. Recently, the relationship between phenylketonuria and biopterin was reported in *Annals of Neurology*, Vol. 3, pp. 224–230 (1978), *The New England Journal of Medicine*, Vol. 299, pp. 673–679 (1978) and *Clinica Chimica Acta*, Vol. 93, pp. 251–262 (1979). Thus, much interest has been shown in the quantitative change of pterins (2-amino-4-hydroxypteridine derivatives) in the human body.

A bioassay method for the determination of biopterin (i.e., 2-amino-4-hydroxy-6-(L-erythro-1,2-dihydroxypropyl)pteridine) is known, as described in *Methods in Enzymology*, Vol. 18 B, p. 618 (1971), however, this method is not suitable for practical use, because it requires a comparatively long time to obtain the result. A method for the determination of neopterin (i.e., 2-amino-4-hydroxy-6-(L- or D-erythro-1,2,3-trihydroxypropyl)pteridine) has not yet been proposed, but it may become necessary in future.

SUMMARY OF THE INVENTION

A primary object of the present invention is to provide pterin derivatives of the formula (I)

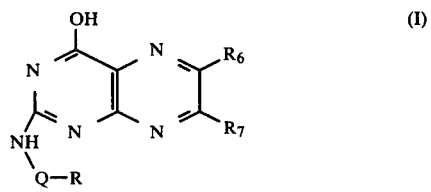

wherein R represents a hydroxyphenyl group, a radio-iodinated hydroxyphenyl group, a tyraminocarbonyl group, a radioiodinated tyraminocarbonyl group, a proteino-carbonyl group or a carboxyl group; Q represents a straight or branched chain alkylene group having from 1 to 6 carbon atoms; and $R_6$ and $R_7$ each represents a hydrogen atom, an alkyl group having from 1 to 6 carbon atoms or a hydroxyalkyl group having from 1 to 6 carbon atoms.

Another object is the use of certain radio-iodinated pteridine derivatives as tracers in a radio-immunoassay (RIA) method.

DETAILED DESCRIPTION OF THE INVENTION

Figure 1:
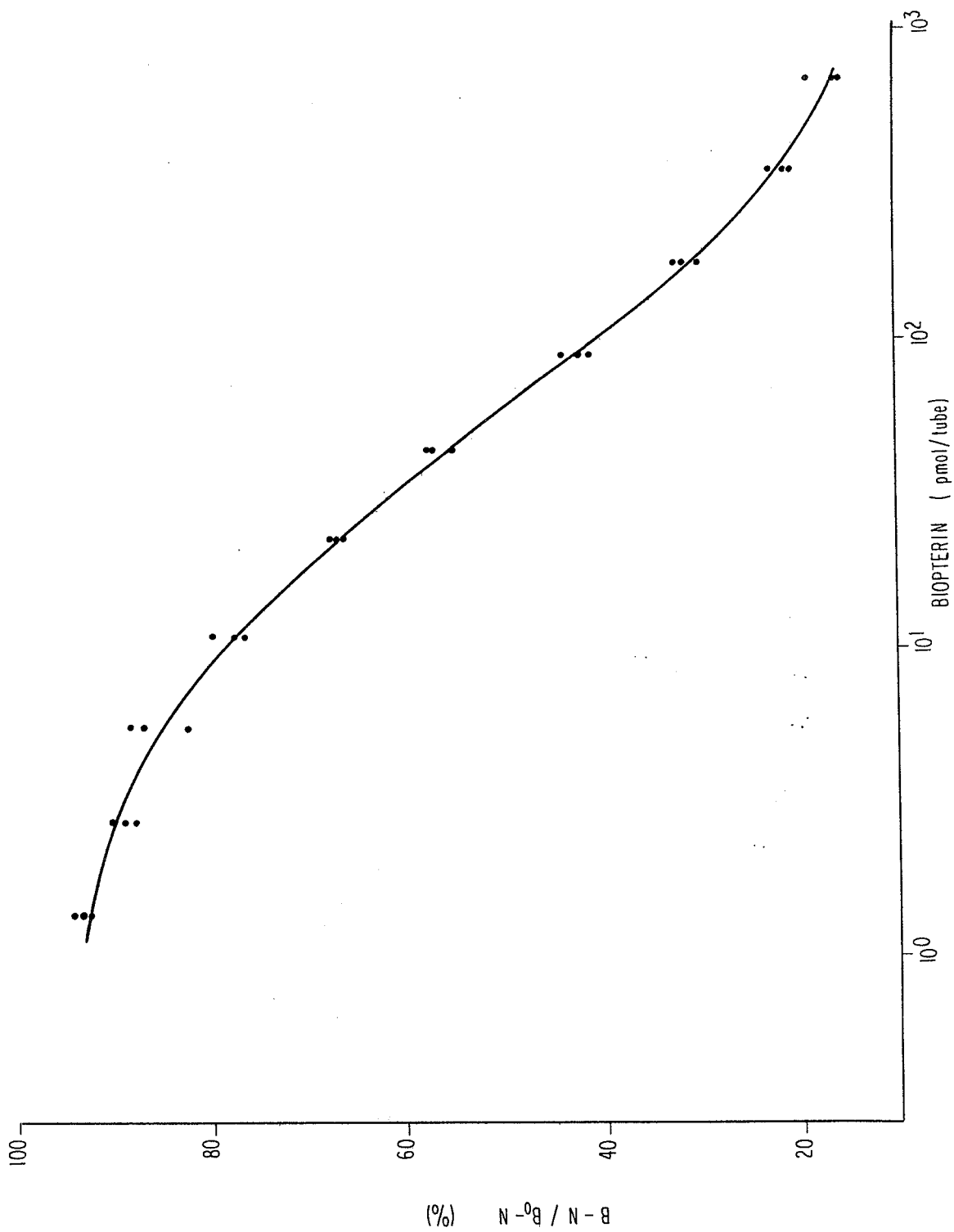
FIGS. 1 and 2 show standard curves for biopterin, where "B" represents the radioactivity (count per minute, hereinafter "cpm"), "Bo" represents the radioactivity (cpm) in the absence of the standard substance (biopterin), and "N" represents the radioactivity of non-specific binding (cpm) in the absence of the antiserum and the standard substance (biopterin).

For the RIA of pterins, two kinds of tracers were synthesized. One was radioiodinated 4-hydroxy-2-tyraminocarbonylalkylaminopteridine derivatives, and the other was radioiodinated 4-hydroxy-2-tyraminopteridine derivatives, and the former has a radioiodinated tyraminocarbonyl group, and the latter has a radioiodinated hydroxyphenyl group, as R in the formula (I). Representative examples of these tracers are radioiodinated 2-[5-(tyraminocarbonyl)pentylamino]-4-hydroxy-6-(L-erythro-1,2-dihyroxypropyl)pteridine and radioiodinated 4-hydroxy-2-[2-(4-hydroxyphenyl)ethyl]-amino-6-(L-erythro-1,2-dihydroxypropyl)pteridine.

Furthermore, novel proteinocarbonylalkylpterins, such as biopterinylcaproylprotein, can also be prepared for antibody production.

Synthesis of the compounds of this invention is illustrated schematically below. In the scheme, biopterin, bovine serum albumin (BSA) and pentylene are used as examples of the pterin, the protein and the alkylene group in the formula (I), respectively,

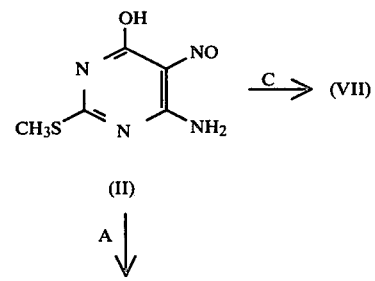

-continued
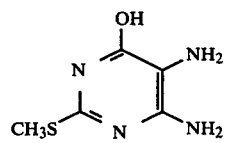
(III)
B ↓
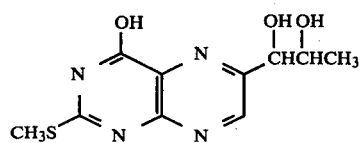
(IVa)
C ↓
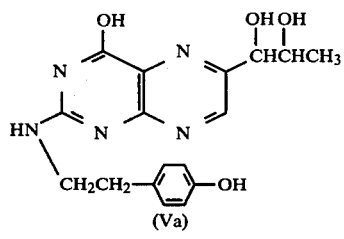 →D→ 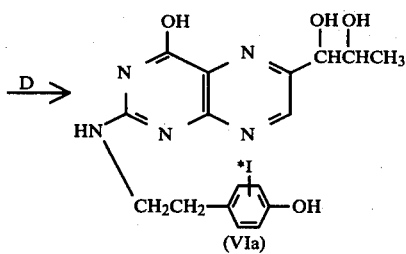
(Va)  (VIa)
(II) →C→ 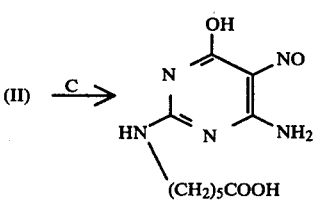
(VII)
A ↓
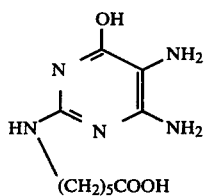
(VIII)
B ↓

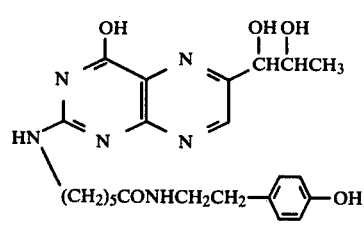

(Xa)

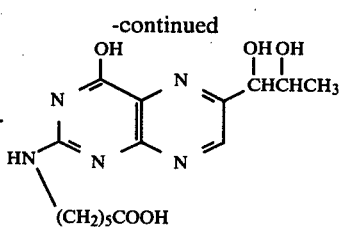

(IXa)

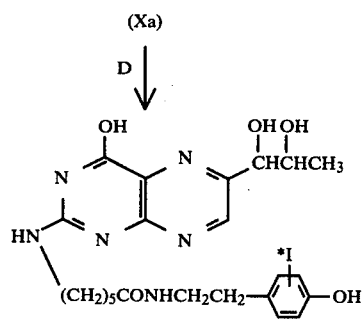

(XIa)

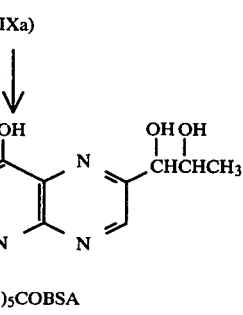

(XIIa)

wherein *I refers to radioactive iodine.

In the above scheme, reactions indicated by the same capital letter neighboring arrow are carried out under substantially the same reaction conditions.

In the reaction scheme, 4-amino-6-hydroxy-2-methylthio-5-nitrosopyrimidine (II) is heated with epsilonaminocaproic acid (an amino acid) in water whereby 4-amino-2-(2-carboxypentylamino-6-hydroxy-5-nitrosopyrimidine (VII) is produced. If the amino acid is an α-amino acid, the reaction is preferably carried out under alkaline condition, e.g., in a 0.25 M aqueous sodium hydroxide solution. When the compound of the formula (II) or (VII) is catalytically reduced, the 5-nitroso group is converted to an amino group to yield the compound of the formula (III) or (VIII), respectively. For the catalytic reduction, palladium-carbon and the like can be used as the catalyst. Then, the compound of the formula (III) or (VIII), after optionally being purified, is heated with 5-deoxyarabinose phenylhydrozone in a solvent to form a pteridine nucleus by ring closure condensation, to produce the compound of the formula (IVa) or (IXa). Examples of solvents are aqueous alcohols and the like and the reaction is preferably carried out under an inert gas stream such as nitrogen. When the compound of formula (IVa) is treated with tyramine by a similar manner to the reaction between the compound (II) and the amino acid described above, 4-hydroxy-6-(1,2-dihydroxypropyl)-2-[2-(4-hydroxyphenyl)ethylamino]pteridine of the formula (Va) is synthesized which can then be labeled with a radioactive iodine as described below and the resulting radioiodinated compound of the formula (VIa) is used as a tracer.

The compound of the formula (IXa) prepared above can then be conjugated with tyramine or a protein such as bovine serum albumin (BSA), rabbit serum albumin or human serum albumin by a method of forming acid-amide bond known in the art. An example of the method is the mixed acid anhydride method, in which an acid [such as the compound (IXa)] is treated with a chloroformic acid ester in the presence of a tertiary amine to yield a mixed anhydride which is then reacted with tyramine or a protein.

Compounds having tyramine in the structure such as (Va) or (Xa) are labeled with a radioactive iodine to produce a tracer by any one of known procedures, preferably, using a modification of the chloramine T (sodium p-toluenesulfonchloramide) procedure, which is well known in the art.

In the general procedure of the chloramine T method, the reaction of the tyramine conjugate with radioactive sodium iodide is allowed to proceed in the presence of chloramine T for from about 30 seconds to about 5 minutes and stopped by addition of sodium metabisulfite. From the standpoint of availability, half-life and specific activity, $^{125}I$ and $^{131}I$ are preferred, with $^{125}I$ being most preferred.

Another procedural route can also be used for the production of the tracer. In this alternative route, tyramine is previously labeled with iodine as described above and subsequently conjugated with a pteridine derivative by using the same reactions as described above.

Of course, the procedure illustrated in the above reaction scheme and described above can be modified by one skilled in the art so that a suitable compound can be prepared in accordance with the particular purpose. For example, in the production of a neopterin compound, D- or L-arabinose phenylhydrazone may be used for the ring-closure reaction in step B. Other examples of a reactant which can be used in this step are diacetyl and glyoxal. Also, compounds of the formula (I) having various alkylene groups can be prepared and examples of such alkylene groups are methylene, ethylene, propylene, butylene and pentylene which may have a substituent such as a methyl, ethyl or hydroxybenzyl group.

For the production of antiserum to the pteridine, known immunization procedures can be employed. For example, mammals are immunized by injection of a protein conjugated pteridine in a form of emulsion with complete Freund's adjuvant. Examples of mammals that can be conveniently used include rabbits, goats, sheep, Guinea pigs, and the like. After several booster injections, blood is collected, followed by removal of the blood corpuscles. The antiserum can be used as is for assay procedure, but purification methods such as salting out or affinity chromatography may first be employed.

Prior to RIA, a urine sample or the like may be pretreated, if necessary, for the RIA procedure. For example, in determining biopterin in urine, the reduced-type biopterin, i.e., dihydrobiopterin and tetrahydrobiopterin, can be oxidized using a suitable oxidizing agent, such as iodine.

The RIA for determining pterins can be performed by a manner known in the art. For example, in one embodiment, the antiserum is diluted to a suitable concentration with a buffer and incubated with a sample solution or a standard solution. The resulting mixture is then incubated with a tracer obtained by the process described above at a suitable temperature, e.g., at room temperature, and then a suitable separation procedure for separating the bound antibody and the free is performed. Examples of such separation procedures include the double antibody method, the dextran-charcoal method, the solid phase method, etc., which are well known in the art. The radioactivity of each one of the separated substances is counted by a well-type scintillation counter and a standard curve is drawn based on the value obtained for the standard solutions and then the urine level is determined based on the standard curve.

The cross-reactivity of the biopterin antiserum with tetrahydrobiopterin, dihydrobiopterin, neopterin, 6,7-dimethylpterin, pterin or folic acid has been found to be negligibly low. The antibody to neopterin or dimethylpterin has also high selectivity, showing little cross-reaction with other pterins.

The RIA method using the tracer and pterinyl-protein of this invention is excellent in accuracy and requires a shorter period, for instance, than the bioassay method reported in *Methods in Enzymology*, Vol. 18 B, p. 618 (1971). The use of a radioiodinated 2-[2-(4-hydroxyphenyl)ethyl]aminopteridine derivative as a tracer gives especially better results in sensitivity than does the use of one of the radioiodinated 2-(tyraminocarbonylalkylamino)pteridines, because the former has a bridge different from that of the antigen (protein conjugate).

In the RIA of a low molecular weight substance which cannot produce antibody by itself (i.e., a hapten), immunization is achieved by administration of a hapten-protein conjugate to mammals. The antiserum thus produced contains an antibody to the bridge moiety as well as the antibody to the hapten. Under such circumstances, it is assumed that when a labeled hapten (tracer) having the same bridge as that contained in the hapten-protein conjugate is used, the assay system exhibits a tendency towards relatively high non-specific bindings and relatively low sensitivity.

If the tracer and the antigen have the same bridge, e.g., caproyl, propionyl, butyryl, a step for removing the antiserum to the bridge is required.

The present invention is further illustrated in greater detail by the following Examples, but they are not to be construed as limiting the present invention. Unless otherwise indicated, all parts, percents, ratios and the like are by weight.

EXAMPLE 1—1

In 500 ml of a 0.5 M aqueous potassium hydroxide solution, 18 g of 4-amino-6-hydroxy-2-methylthio-5-nitrosopyrimidine (II) was dissolved. 10 g of 5% palladium-carbon was added to the solution and reduction was performed at room temperature under normal atmospheric pressure until the theoretical amount of hydrogen was consumed. After removal of the catalyst by filtration, the filtrate was adjusted to a pH of 3 to 4, using formic acid, whereby 4,5-diamino-6-hydroxy-2-methylthiopyrimidine (III) was precipitated as colorless needles. Without isolation, the crystals were added to a mixture of 32 g of 5-deoxy-L-arabinose phenylhydrazone and 400 ml of methanol, and the resulting mixture was stirred under nitrogen gas at 25° C. for 90 minutes and under reflux for another 30 minutes. The resulting mixture was cooled in an ice bath, and 100 g of potassium hexacyanoferrate (III) as well as aqueous potassium iodide solution (5 g/500 ml) were added thereto. The mixture was stirred at a pH of 3 to 4 at 25° C. for 20 hours while introducing oxygen therein, and the reaction mixture was concentrated in vacuo to a volume of 500 ml and adjusted to a pH of 9 to 10 with ammonia. Non-fluorescent solid was removed by filtration and the filtrate was passed through a Florisil column (5 × 60 cm) and eluted with water. Two fractions having blue fluorescence were obtained. The main fraction was concentrated to 150 ml and treated again with a Florisil column and elution. The eluate was concentrated in vacuo to dryness, and the residue was extracted with 500 ml of hot methanol. The extract was concentrated to a volume of 50 ml, which upon cooling yielded 5.5 g of colorless needles of 4-hydroxy-6-(L-erythro-1,2-dihydroxypropyl)-2-methylthiopteridine (IVa). This product decomposed at a temperature above 210° C. (recrystallized from water).

Elementary Analysis: Calcd. for $C_{10}H_{12}N_4O_3S.2H_2O$: C, 39.46; H, 5.31; N, 18.41. Found: C, 40.27; H, 4.45; N, 18.65.

In the same manner as described above, but using D- or L-arabinose phenylhydrazone instead of 5-deoxy-L-arabinose phenylhydrazone, 4-hydroxy-6-(D-erythro-1,2,3-trihydroxypropyl)-2-methylthiopteridine (IVb) or the L-form (IVc) thereof were obtained, respectively. The decomposition point of both isomers after crystallization from water was 158° C.

Elementary Analysis: Calcd. for $C_{10}H_{12}N_4O_4S.H_2O$: C, 39.72; H, 4.68; N, 18.54. Found for D-form: C, 39.63; H, 4.68; N, 18.03. Found for L-form: C, 39.75; H, 4.63; N, 18.17.

EXAMPLE 1—2

A mixture of 1.0 g of 4-hydroxy-6-(L-erythro-1,2-dihydroxypropyl)-2-methylthiopteridine (IVa), 3.0 g of tyramine, 0.8 g of acetic acid and a 50% aqueous solution of 2-methoxyethanol was heated at a temperature in the range of 100° to 105° C. for 6 hours. The pH of the reaction mixture was adjusted to 1 to 2 with hydrochloric acid and the mixture was passed through a Florisil column (3.5 × 40 cm) and the unreacted starting materials were removed by washing the column with 500 ml of a 2 M aqueous formic acid solution next with 500 ml of water and then the product was eluted gradiently with 1,000 ml of aqueous ammonia solutions having an ammonia concentration from 0 to 2%. The eluate was concentrated to a volume of 150 ml and treated again using a Florisil column as before. The eluate was concentrated to dryness, extracted with 200 ml of an aqueous ammonia solution, and the extract was concentrated to a volume of 100 ml. The pH of the mixture was adjusted to 3 to 4 with formic acid, and the mixture was cooled to obtain 4-hydroxy-2-[2-(4-hydroxyphenyl)ethyl]amino-6-(L-erythro-1,2-dihydroxypropyl)pteridine (Va) as yellow needles decomposing at 165° C. (crystallized from water).

Elementary Analysis: Calcd. for $C_{17}H_{19}N_5O_4.H_2O$: C, 54.39; H, 5.64; N, 18.66. Found: C, 54.56; H, 5.62; N, 18.38.

EXAMPLE 1—3

Labeling with Radioactive Iodine

To 20 μl of a 0.05 M phosphate buffer (pH 7.4), 10 μl of dimethylformamide containing 10 μl of the compound (Va) obtained as described in Example 1-2 was added and 10 μl (1.2 mCi) of Na $^{125}I$ was added thereto followed by addition of 20 μg of chloramine T dissolved in 10 μ l of the same buffer. The resulting mixture was allowed to react at 25° C. for 30 seconds. The reaction was stopped by addition of 40 μg of sodium metabisulfite dissolved in 10 μ l of the same buffer. The resulting reaction mixture was purified by electrophoresis on cellulose acetate separating with a 0.05 M phosphate buffer (pH 7.6) and extracted with a phosphate buffer containing BSA at a concentration of 5% whereby $^{125}$I-labeled 4-hydroxy-2-[2-(4-hydroxyphenyl)ethyl]amino-6-(L-erythro-1,2-dihydroxypropyl)pteridine (VIa) was obtained. Rf 0.48 [silica gel thin layer; ethyl acetatemethanol-5% aqueous ammonia solution (1:1:0.2)] v/v.

EXAMPLE 1—4

Production of Standard Substances

A mixture of 0.2 g of 4-hydroxy-6-(L-erythro-1,2-dihydroxypropyl)-2-methylthiopteridine )IVa), 0.6 g of ammonium acetate and 5 ml of concentrated aqueous ammonium solution was heated under reflux for 4 hours. The reaction mixture was acidified to a pH of 2 with hydrochloric acid, and passed through a Florisil column (3.5×20 cm) which was then eluted with water. The eluate was concentrated to dryness in vacuo. The residue was extracted with 50 ml of an aqueous ammonia solution and the extract was concentrated to 10 ml and cooled whereby 90 mg of biopterin was obtained as ivory-colored needles, whose physiochemical properties were identical to those of the authentic samples.

In a manner similar to the above, D-erythroneopterin (60% yield) and L-erythro-neopterin (72% yield) were obtained from the corresponding 2-methylthio compounds (IVb) and (IVc), respectively.

EXAMPLE 2

10 g of 4-amino-6-hydroxy-2-methylthio-5-nitrosopyrimidine (II) and 20 g of epsilonaminocaproic acid were added to 400 ml of water, and the mixture was heated under reflux for 1 hour. The reaction mixture, which was adjusted to a pH of 2 to 3 using formic acid, was cooled and the precipitate was collected by filtration to obtain 8.5 g of 4-amino-2-(5-carboxypentylamino)-6-hydroxy-5-nitrosopyrimidine (VII). When this product was dissolved in hot diluted aqueous ammonia solution and acidified with formic acid, reddish-orange needles were obtained.

The compounds of the formula (VII) obtained through a procedure similar to the above as well as the melting points thereof and the starting materials used are shown in Table 1.

TABLE 1

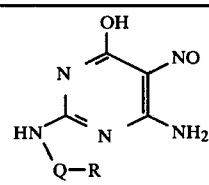

| Q—R | m.p. (°C.) | Starting Material |
|---|---|---|
| $CH_2COOH$ | 300, turned black at 280 | glycine |
| $(CH_2)_2COOH$ | 300 | β-alanine |
| $(CH_2)_3COOH$ | 240–241 (dec.) | γ-aminobutyric acid |
| $(CH_2)_5COOH$ | 232.5–233.5 (dec.) | ε-aminocaproic acid |
| $CH(CH_3)COOH(1S)$ | 300, turned black at 245 | L-alanine |
| $CH(CH_3)COOH(1R)$ | 300 | D-alanine |
| CH(COOH)CH$_2$—⟨⟩—OH | 300 | L-tyrosine |

EXAMPLE 3—1

4.3 g of 4-amino-2-(5-carboxypentylamino)-6-hydroxy-5-nitrosopyrimidine (VII) was added to 60 ml of a 2 M sodium hydroxide solution and catalytically reduced with hydrogen in the presence of 2 g of palladium-carbon. After absorption of hydrogen ceased, 20 ml of concentrated hydrochloric acid was added to the reaction mixture and the catalyst was removed by filtration. The filtrate was concentrated and the resulting crystals were dried using phosphorus pentoxide as a desiccant to obtain 9.5 g of 4,5-diamino-2-(5-carboxypentylamino)-6-hydroxy-pyrimidine dihydrochloride monohydrate (VIII). 5.0 g of the product thus-obtained and 3.7 g of 5-deoxy-L-arabinose phenylhydrazone were added to 400 ml of 50% (v/v) methanol and the mixture was refluxed under a nitrogen stream for 20 minutes. The pH of the reaction mixture was adjusted to 5, and air was introduced into the mixture for 6 hours. The reaction mixture was concentrated to dryness, 100 ml of water was added thereto and the pH of the mixture was adjusted to 2.0 with formic acid. The mixture was passed through a Florisil column (400 ml) washed with 0.25 M formic acid and eluted with water. The eluate was concentrated to dryness, extracted with 250 ml of methanol and the extract was concentrated to dryness. The residue was crystallized from 10 ml of ethanol to give 465 mg of 2-(5-carboxypentylamino)-4-hydroxy-6-(L-erythro-1,2-dihydroxypropyl)pteridine (IXa).

Elementary Analysis: Calcd. for $C_{15}H_{21}N_5O_5.H_2O$: C, 48.77; H, 6.28; N, 18.96. Found: C, 48.55; H, 6.25; N, 18.55.

EXAMPLE 3-2

4.3 g of 4,5-diamino-2-(5-carboxypentylamino)-6-hydroxypyrimidine dihydrochloride monohydrate and 2.5 g of diacetyl were dissolved in 100 ml of water and, after adjusting the pH to 2 to 3, the solution was heated under reflux for 1 hour. After cooling, the precipitate was crystallized from 50% (v/v) methanol, and 3.1 g of 2-(5-carboxypentylamino)-4-hydroxy-6,7-dimethylpteridine was obtained as yellow needles having an m.p. 215°–219° C. (dec.).

EXAMPLE 4-1

74 mg of 2-(5-carboxypentylamino)-4-hydroxy-6-(L-erythro-1,2-dihydroxypropyl)pteridine and 126 μl of triethylamine were added to 2 ml of dimethylformamide (DMF). To the mixture was added 65 μl of ethyl chloroformate while cooling to −5° C. and the mixture was stirred for 15 minutes. After addition of 2 ml of a DMF solution containing 52 mg of tyramine, the mixture was stirred at a temperature of −5° C. for 30 minutes and then at 0° C. for 1 hour. The reaction mixture was concentrated in vacuo and 3 ml of 1 M sodium hydroxide was added to the residue and the mixture was allowed to stand at 30° C. for 30 minutes. The reaction mixture was acidified with formic acid and purified by Florisil column chromatography (column 100 ml, eluted with ethanol-water), and then the product was crystallized from water to give 66 mg of 2-(5-carboxypentylamino)-4-hydroxy-6-(L-erythro-1,2-dihydroxypropyl)pteridine-tyramine conjugate (biopterinylcaproyltyramine) (Xa) as colorless needles with m.p. 169°–171° C. (dec.).

Elementary Analysis: Calcd. for $C_{23}H_{30}N_6O_5 \cdot H_2O$: C, 56.54; H, 6.60; N, 17.20. Found: C, 56.65; H, 6.48; N, 17.34.

EXAMPLE 4-2

184 mg of 2-(5-carboxypentylamino)-4-hydroxy-6-(L-erythro-1,2,3-trihydroxypropyl)pteridine and 400 μl of triethylamine were dissolved in 2 ml of DMF and then 200 μl of ethyl chloroformate was added thereto at a temperature of −5° C. The mixture was stirred at −5° C. for 15 minutes and added to 2 ml of a DMF solution of 137 mg of tyramine. The resulting mixture was stirred at −5° C. for 30 minutes, at 0° C. for 1 hour and at room temperature for 30 minutes. The reaction mixture was concentrated in vacuo and 2 ml of 1 M sodium hydroxide was added thereto. After allowing to stand at room temperature for 30 minutes, the mixture was acidified with formic acid and purified by Florisil column chromatography (column 100 ml) eluting with ethanol-water to give 101 mg of 2-(5-carboxypentylamino)-4-hydroxy-6-(L-erythro-1,2,3-trihydroxypropyl)pteridine-tyramine conjugate (a neopterinylcaproyltyramine), m.p. 192°–196° C. (dec.) (crystallized from aqueous ethanol).

Elementary Analysis: Calcd. for $C_{23}H_{30}N_6O_6 \cdot H_2O$: C, 54.75; H, 6.39; N, 16.66. Found: C, 54.94; H, 6.40; N, 16.33.

EXAMPLE 4—3

249 mg of 2-(5-carboxypentylamino)-4-hydroxy-6,7-dimethylpteridine and 200 μl of triethylamine were added to 4 ml of DMF and then 100 μl of ethyl chloroformate was added thereto at a temperature of −5° C. The mixture was allowed to react at −5° C. for 15 minutes. After addition of 2 ml of a DMF solution containing 205 mg of tyramine, reaction was carried out with stirring at −5° C. for 30 minutes and at room temperature for 1 hour. The reaction mixture was concentrated in vacuo and the residue was dissolved in water. After acidification with formic acid, the mixture was purified by Florisil column chromatography, eluting gradiently using 1 l of water and 1 l of an aqueous solution containing 200 ml of acetone and 4 g of ammonia to give 209 mg of 2-(5-carboxypentylamino)-4-hydroxy-6,7-dimethylpteridinetyramine conjugate, m.p. 200° C. (dec.) (crystallized from 50% (v/v) ethanol).

Elementary Analysis: Calcd. for $C_{22}H_{28}N_6O_3 \cdot H_2O$: C, 59.71; H, 6.83; N, 18.99. Found: C, 59.77; H, 7.35; N, 18.76.

EXAMPLE 5

Labeling with Radioactive Iodine

10 μl of DMF containing 10 μg of biopterinylcaproyltyramine conjugate was added to 20 μl of a 0.05 M phosphate buffer (pH 7.4), and to the mixture were added 10 μl (1.2 mCi) of $Na^{125}I$ and then 20 μg of choramine T dissolved in 10 μL of the same buffer. The mixture was allowed to react at 25° C. for 30 seconds and the reaction was stopped by addition of 40 μg of sodium metabisulfite dissolved in 10 μl of the same buffer. The product was purified by electrophoresis on cellulose acetate, separated with a 0.05 M phosphate buffer (pH 7.6) and extracted with a phosphate buffer containing 0.5% BSA to obtain $^{125}I$-labeled 2-(5-carboxypentylamino)-4-hydroxy-6-(L-erythro-1,2-dihydroxypropyl)pteridine-tyramine conjugate. Rf 0.50 [silica gel TLC; ethyl acetate-methanol-5% aqueous ammonia solution (1:1:0.2)]v/v.

EXAMPLE 6—1

Conjugation with BSA 74 mg of biopterinylcaproyltyramine and 168 μl of triethylamine were added to 1 ml of DMF and 87 μl of ethyl chloroformate was then added thereto at a temperature of −5° C. The mixture was stirred for 15 minutes and added to a mixture of 114 mg of bovine serum albumin (BSA), 2 ml of water and 200 μl of a 1 M sodium hydroxide solution. The resulting mixture was then stirred at −5° C. while adjusting its pH to 9 for 30 minutes, at 0° C. for 1 hour and at room temperature for 1 hour. After addition of 5 ml of 1 M sodium hydroxide, the mixture was allowed to stand at room temperature for 30 minutes then dialysed using a cellophane tube against running water. The cellophane tube was put into a beaker containing a mixture of 1 g of sodium acetate and 300 ml of water, adjusted to the pH of 4.5, and dialysed for 6 hours. The inner solution was then centrifuged and the precipitate was lyophilized to obtain 95 mg of 2-(5-carboxypentylamino)-4-hydroxy-6-(L-erythro-1,2-dihydroxypropyl)pteridine-BSA conjugate (biopterinylcaproyl-BSA).

EXAMPLE 6—2

73.4 mg of 2-(5-carboxypentylamino)-4-hydroxy-6-(L-erythro-1,2,3-trihydroxypropyl)pteridine and 168 μl of triethylamine were added to 1 ml of DMF and then 87 μl of ethyl chloroformate was added thereto at a temperature of −5° C., followed by stirring the mixture for 15 minutes. The reaction solution was added to a mixture of 114 mg of BSA, 2 ml of water and 200 μl of 1 M sodium hydroxide, and the resulting mixture was then stirred at −5° C. while adjusting the pH to 9 for 30 minutes, then at 0° C. for 1 hour, and at room temperature for 1 hour. After addition of 1 M sodium hydroxide, the mixture was allowed to stand at room temperature for 30 minutes. The reaction mixture was dialysed in a manner as described in Example 6—1, centrifuged, and the precipitate was lyophilized to obtain 100 mg of 2-(5-carboxypentylamino)-4-hydroxy-6-(L-erythro-1,2,3-trihydroxypropyl)pteridine-BSA conjugate (a neopterinylcaproyl-BSA).

In a procedure similar to that described above, the following BSA-conjugates were obtained.

EXAMPLE 6—3

2-(5-carboxypentyl)amino-4-hydroxy-6,7-dimethylpteridine-BSA conjugate (83 mg) from 61 mg of 2-(5-carboxypentylamino)-4-hydroxy-6,7-dimethylpteridine. Substitution ratio of pterin: 82% [calculated from $\Delta\epsilon_{350}$ (pH 7.0)].

EXAMPLE 6—4

2-carboxymethylamino-4-hydroxy-6-(L-erythro-1,2,3-trihydroxypropyl)pteridine-BSA conjugate (44 mg) from 31 mg of the corresponding 2-carboxymethylamino compound.

EXAMPLE 6—5

2-carboxymethylamino-4-hydroxy-6,7-dimethylpteridine-BSA conjugate (32 mg) from 25 mg of the corresponding 2-carboxymethylamino compound.

The substances obtained as in from Example 1—2 to Example 6—5 or through a similar procedure thereto are listed in the following Table 2 in connection with formula (I) shown above.

TABLE 2

| Q—R | $R_6$ | $R_7$ | m.p. (°C.) or Rf |
|---|---|---|---|
| CH₂CH₂—⟨phenyl⟩—OH | DHP | H | 165 (d) |
| " | THP(D) | " | 180–182 (d) |
| " | THP | " | 182–184 (d) |
| CH₂CH₂—⟨phenyl-$^{125}$I⟩—OH | DHP | " | Rf 0.48 |
| $CH_2COOH$ | Me | Me | 206–210 (dec.) |
| $(CH_2)_2COOH$ | " | " | 275 (turned black) |
| $(CH_2)_3COOH$ | " | " | 238–240 (dec.) |
| $(CH_2)_5COOH$ | " | " | 215–219 (dec.) |
| $CH(CH_3)COOH(1S)$ | " | " | 193–194 (dec.) |
| $(CH_2)_5COOH$ | DHP | H | 216–218 (dec.) |
| $CH_2COOH$ | THP | " | 177–180 (dec.) |
| $(CH_2)_5COOH$ | " | " | 186–190 (dec.) |
| $(CH_2)_5CO$—tyramine | $CH_3$ | $CH_3$ | 200 (dec.) |
| " | THP | H | 192–196 (dec.) |
| " | DHP | " | 169–171 (dec.) |
| $(CH_2)_5CO$—BSA | Me | Me | |
| " | THP | H | |
| " | DHP | " | |
| $CH_2CO$—BSA | Me | Me | |
| " | THP | H | |
| $(CH_2)_5CO$—tyramine-$^{125}$I | Me | Me | Rf 0.58 |
| " | THP | H | Rf 0.36 |
| " | DHP | " | Rf 0.50 |

DHP: L-erythro-1,2-dihydroxypropyl
THP: L-erythro-1,2,3-trihydroxypropyl
THP(D): D-erythro-1,2,3-trihydroxypropyl
RF was the value on silica gel thin layer developed with ethyl acetate-methanol-5% aqueous ammonia solution (1:1:0.2)v/v.

EXAMPLE 7

Production of Antibody 2-(5-carboxypentylamino)-4-hydroxy-6-(L-erythro-1,2-dihydroxypropyl)pteridine-BSA conjugate with complete Freund's adjuvant was injected intradermally into New Zealand white rabbits (1 mg per rabbit). After 1 month, additional immunization (0.4 mg per rabbit) was performed in the same manner, and total four times of the additional immunization were made in weekly interval. 10 days after the final immunization, blood was collected from the rabbits, and antiserum was obtained therefrom.

EXAMPLE 8—1

(a) Pretreatment of urine sample

To 5.0 ml of fresh human urine, 500 μl of 5 M hydrochloric acid and 1 ml of a 0.2% $I_2$–0.4% KI solution were added and the resulting mixture was allowed to stand at room temperature for 1 hour. Then, the same treatment, except using 0.5 M sodium hydroxide instead of the hydrochloric acid, was carried out. The oxidation reaction was stopped by the addition of 0.5 ml of 2% ascorbic acid and the reaction mixture was centrifuged at 7,000 rpm for 15 minutes. The supernatant was subjected to a column of Dowex-50(H+) (0.9×2 cm). After washing the column with 20 ml of water, biopterin was eluted with 5 ml of 1 M aqueous ammonium solution. The eluate was adjusted to pH 7.0 and to a volume of 6.0 ml with 250 μl of a 0.5 M phosphate buffer (pH 7.0) and 5 M hydrochloric acid, and was then used for assay. (b) RIA of biopterin In the assay procedure, a 0.0175 M phosphate buffer containing 0.1% BSA was used.

To remove the antibody to the caproic acid moiety, two series of the mixture of 10 μg of 2-(5-carboxypentylamino)-4-hydroxy-6-(L-erythro-1,2-dihydroxypropyl)pteridine and 100 μl of 800-fold diluted antiserum were incubated at 37° C. for 30 minutes. To one series of the resulting solution was added 100 μl of the buffer containing standard biopterin (0 to 710 pmol) and to another series of the solution was added 100 μl of the diluted sample urine (4, 8, 16 and 32-fold dilution), and the mixtures were incubated at 37° C. for 30 minutes. To each of them, 10 μl of radioiodinated ($^{125}$I) 2-(5-carboxypentylamino)-4-hydroxy-6-(L-erythro-1,2-dihydroxypropyl)pteridine-tyramine conjugate (20,000 cpm) was added, and the mixture was allowed to stand at room temperature for 30 minutes. Then, 100 μl of anti-rabbit IgG was added thereto as the second antibody followed to stand at room temperature for 15 minutes. After addition of 500 μl of 4% dextran T-70 (Pharmacia), the mixture was vigorously mixed and centrifuged at 2,000 rpm at 4° C. for 15 minutes. Then the radioactivity of each precipitate was counted. A standard curve (FIG. 1) was drawn by plotting the value (B-N/$B_o$-N) obtained on standard solutions, then biopterin levels in sample urine were determined based on the curve, which are shown in Table 3 in comparison with the levels obtained by the bioassay described previously.

TABLE 3

| No. of Sample | Biopterin (n mol/ml urine) | |
|---|---|---|
| | RIA | Bioassay |
| 1 | 5.75 | 5.4 |
| 2 | 15.1 | 16.0 |
| 3 | 8.0 | 7.2 |
| 4 | 10.7 | 8.9 |
| 5 | 9.7 | 8.9 |

EXAMPLE 8—2

(a) Pretreatment of urine sample

To 500 μl of fresh human urine was added 50 μl of a 2 M hydrochloric acid and 50 μl of a 2% $I_2$-4% KI solution, and the mixture was allowed to stand at room temperature in the dark for 1 hour. Then, the oxidation was stopped by addition of 50 μl of a 2% ascorbic acid solution to the mixture. The reaction mixture was lyophilized to remove hydrochloric acid, and the residue was dissolved in 0.02 M phosphate buffer (pH 7.5) containing 0.3% BSA and used for assay.

(b) RIA of biopterin

In the assay procedure, 0.02 M phosphate buffer (pH 7.4) containing 0.1% BSA was used.

To a mixture of 100 μl of the buffer and 100 μl of antiserum (about 4,000–5,000 fold dilution), 100 μl of standard biopterin (0–300 pmol) in buffer solution or 100 μl of sample urine (50–100 fold dilution) was added. The mixture was incubated at 37° C. for 30 minutes. To each of them, 100 μl of radioiodinated ($^{125}$I) 4-hydroxy-2-[2-(4-hydroxyphenyl)ethyl]amino-6-(L-erythro-1,2-dihydroxypropyl)pteridine (10,000–20,000 cpm) was added and the resulting mixture was allowed to stand at 4° C. for 1 to 2 hours.

To the reaction mixture, 100 μl of anti-rabbit IgG was added as the second antibody. The mixture was allowed to stand at room temperature for 10 minutes and 100 μl of 4% dextran T-70 (Pharmacia) was added thereto. The mixture was vigorously mixed and centrifuged at 2,500 rpm at 4° C. for 15 minutes. Then the radioactivity of the precipitate was counted.

Figure 2:
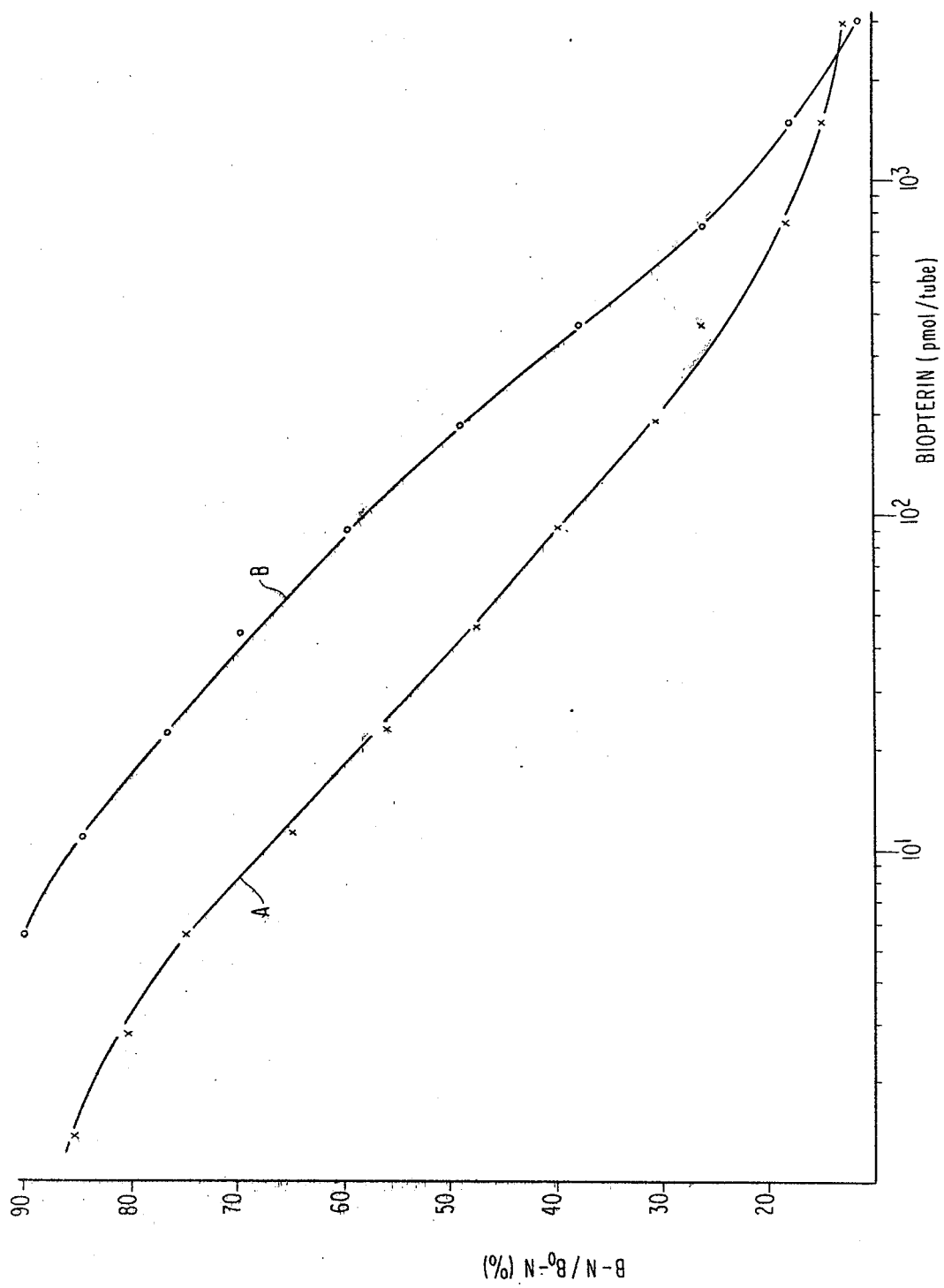

By plotting the values (B-N/$B_o$-N) thus obtained, the standard curve (A) was drawn as shown in FIG. 2 compared with the curve (B) obtained by using the same tracer as in Example 8-1. As seen in the figure the curves express sharp dose response suitable for RIA, and particularly the sensitivity using the tracer having a bridge different from that of antigen is higher than that in the case of using the same bridge.

While the invention has been described in detail and with reference to specific embodiments thereof, it will be apparent to one skilled in the art that various changes and modifications can be made therein without departing from the spirit and scope thereof.

What is claimed is:

1. A compound of the formula

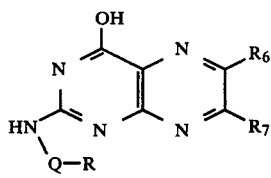

wherein R represents a hydroxyphenyl, a radioiodinated hydroxyphenyl, a tyraminocarbonyl, a radioiodinated tyraminocarbonyl, a proteinocarbonyl group or a carboxyl; Q represents a straight or branched chain alkylene group having from 1 to 6 carbon atoms; and $R_6$ and $R_7$ each represents hydrogen, and alkyl group having from 1 to 6 carbon atoms, or a hydroxyalkyl group having from 1 to 6 carbon atoms.

2. A compound as in claim 1, wherein the compound is radioiodinated 4-hydroxy-2-[2-(4-hydroxyphenyl)ethylamino]-6-(L-erythro-1,2-dihydroxypropyl)pteridine.

3. A compound as in claim 1, wherein the compound is radioiodinated 2-[5-(tyraminocarbonyl)pentylamino]-4-hydroxy-6-(L-erythro-1,2-dihydroxypropyl)pteridine.

4. A compound as in claim 1, wherein the compound is 2-(5-carboxypentylamino)-4-hydroxy-6-(L-erythro-1,2-dihydroxypropyl)pteridine-BSA conjugate.

5. A compound as in claim 1, wherein the compound is 2-(5-carboxypentylamino)-4-hydroxy-6-(L-erythro-1,2-dihydroxypropyl)pteridine.

6. A compound as in claim 1, wherein the compound is radioiodinated 4-hydroxy-2-[2-(4-hydroxyphenyl)ethylamino]-6-(L-erythro-1,2,3-trihydroxypropyl)pteridine.

7. A compound as in claim 1, wherein the compound is radioiodinated 2-[5-(tyraminocarbonyl)pentylamino]-4-hydroxy-6-(L-erythro-1,2,3-trihydroxypropyl)pteridine.

8. A compound as in claim 1, wherein the compound is 2-(5-carboxypentylamino)-4-hydroxy-6-(L-erythro-1,2,3-trihydroxypropyl)-pteridine-BSA conjugate.

9. A compound as in claim 1, wherein the compound is 2-(5-carboxypentylamino)-4-hydroxy-6-(L-erythro-1,2,3-trihydroxypropyl)pteridine.

10. A method of radioimmunoassay for determining pterines, comprising mixing an unknown sample or a known amount of a standard with a labeled compound of the formula

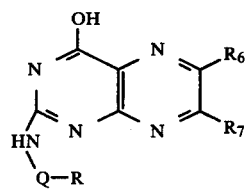

wherein R represents a radioiodinated hydroxyphenyl group or a radioiodinated tyraminocarbonyl group; Q represents a straight or branched chain alkylene group having from 1 to 6 carbon atoms; and $R_6$ and $R_7$ each represents hydrogen, an alkyl group having from 1 to 6 carbon atoms, or a hydroxyalkyl group having from 1 to 6 carbon atoms, and anti-pterines antibody, separating bound labeled compound from remaining free labeled compound, and counting the radiation emitted from either the bound labeled compound or the free labeled compound in a gamma counter.

11. A method of radioimmunoassay for determining pterins as in claim 10 wherein the anti-pterines antibody is prepared by using 2-(5-carboxypentylamino)-4-hydroxy-6-(L-erythro-1,2-dihydroxypropyl)pteridine-BSA conjugate as an antigen.

12. A method of radioimmunoassay for determining pterines as in claim 10 wherein the labeled compound is radioiodinated 4-hydroxy-2-[2-(4-hydroxyphenyl)ethylamino]-6-(L-erythro-1,2-dihydroxypropyl)pteridine.

13. A method of radioimmunoassay for determining pterins as in claim 10 wherein the labeled compound is radioiodinated 2-[5-(tyraminocarbonyl)pentylamino]-4-hydroxy-6-(L-erythro-1,2-dihydroxypropyl)pteridine.

14. A method of radioimmunoassay for determining pterines as in claim 10 wherein the anti-pterines antibody is prepared by using 2-(5-carboxypentylamino)-4-hydroxy-6-(L-erythro-1,2,3-trihydroxylpropyl)pteridine-BSA conjugate as an antigen.

15. A method of radioimmunoassay for determining pterines as in claim 10 wherein the labeled compound is radioiodinated 2-[5-(tyraminocarbonyl)pentylamino]-4-hydroxy-6-(L-erythro-1,2,3-trihydroxypropyl)pteridine.

16. A method of radioimmunoassay for determining pterines as in claim 10 wherein the labeled compound is radioiodinated 4-hydroxy-2-[2-(4-hydroxyphenyl)ethylamino]-6-(L-erythro-1,2,3-trihydroxypropyl)pteridine.

* * * * *